(12) United States Patent
Hatzfeld et al.

(10) Patent No.: US 7,601,534 B1
(45) Date of Patent: Oct. 13, 2009

(54) METHOD FOR MULTIPLYING STEM CELLS

(75) Inventors: Jacques Alexandre Hatzfeld, Antony (FR); Antoinette Hatzfeld, Antony (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 689 days.

(21) Appl. No.: 09/980,484

(22) PCT Filed: May 30, 2000

(86) PCT No.: PCT/FR00/01486

§ 371 (c)(1),
(2), (4) Date: Mar. 25, 2002

(87) PCT Pub. No.: WO00/75290

PCT Pub. Date: Dec. 14, 2000

(30) Foreign Application Priority Data

Jun. 3, 1999 (FR) .................................. 99 07011

(51) Int. Cl.
*C12N 5/00* (2006.01)
*C12N 5/02* (2006.01)
*C12N 5/08* (2006.01)

(52) U.S. Cl. ................. 435/377; 435/366; 435/372; 435/384

(58) Field of Classification Search ........... 435/325, 435/363, 366, 374, 377, 404, 405, 372, 384
See application file for complete search history.

(56) References Cited

U.S. PATENT DOCUMENTS 6,084,060 A * 7/2000 Moore .................. 530/200

FOREIGN PATENT DOCUMENTS

EP 0 834 556 4/1998

OTHER PUBLICATIONS

Xi et al. Br. Journ. Of Haematology, 93:265-272 (1996).*
Thomson. PNAS, 92:7844-7848 (Aug. 1995).*
Williams et al. Nature, 336:684-687 (Dec. 15, 1988).*
Hatzfeld et al. [Exp. Hematology, 25(8):777 (1997), Meeting Abstract No. 174)].*
Fortunel et al. J. of Cell Science, 111: 1867-1875 (1998).*
NIH, Stem Cells: Scientific Progress and Future Research Directions, Chapter 4: The Adult Stem Cell, pp. 23-42, Department of Health and Human Services, Jun. 2001.*
Attisano et al. Cytokine & Growth Factor Reviews, 7(4): 327-339, 1996.*
Chang et al. Endocrine Rev, 23(6): 787-823, 2002.*
Wianny F. et al., "Proliferation and Differentiation of Porcine Inner Cell Mass and Epiblast In Vitro", Biology of Reproduction, Oct. 1997, pp. 756-764.
Hatzfeld J. et al., "Release of Early Human Hematopoietic Progenitors from Quiescence by Antisense Transforming Growth Factor Beta1 or Rb Oligonucleotides", Journal of Experimental Medicine, JP, Toyko, vol. 174, Oct. 1, 1991, pp. 925-929.
Waegell W. et al., "Growth acceleration and stem cell expansion in Dexter-type cultures by neutralization of TGF-beta", Experimental Hematology, vol. 22, 1994, pp. 1051-1057.
Mummery C. et al., "Expression of Transforming Growth Factor beta2 during the Differentiation of Murine Embryonal Carcinoma and Embryonic Stem Cells", Developmental Biology, Jan. 1990, pp. 161-170.
Ducos Karin et al., "p21$^{cip1}$ mRNA Is Controlled by Endogenous Transforming Growth Factor-beta1 in Quiescent Human Hematopoietic Stem/Progenitor Cells", Journal of Cellular Physiology, vol. 184, No. 1, Jul. 2000, pp. 80-85.

* cited by examiner

*Primary Examiner*—Thaian N Ton
(74) *Attorney, Agent, or Firm*—Young & Thompson

(57) ABSTRACT

The use of a cellular development inhibitor in a controlled manner in order to maintain an undifferentiated stem cell state, especially one of human stem cells, whereby cell division is permitted.

4 Claims, 1 Drawing Sheet

METHOD FOR MULTIPLYING STEM CELLS

Figures 1A, 1B:
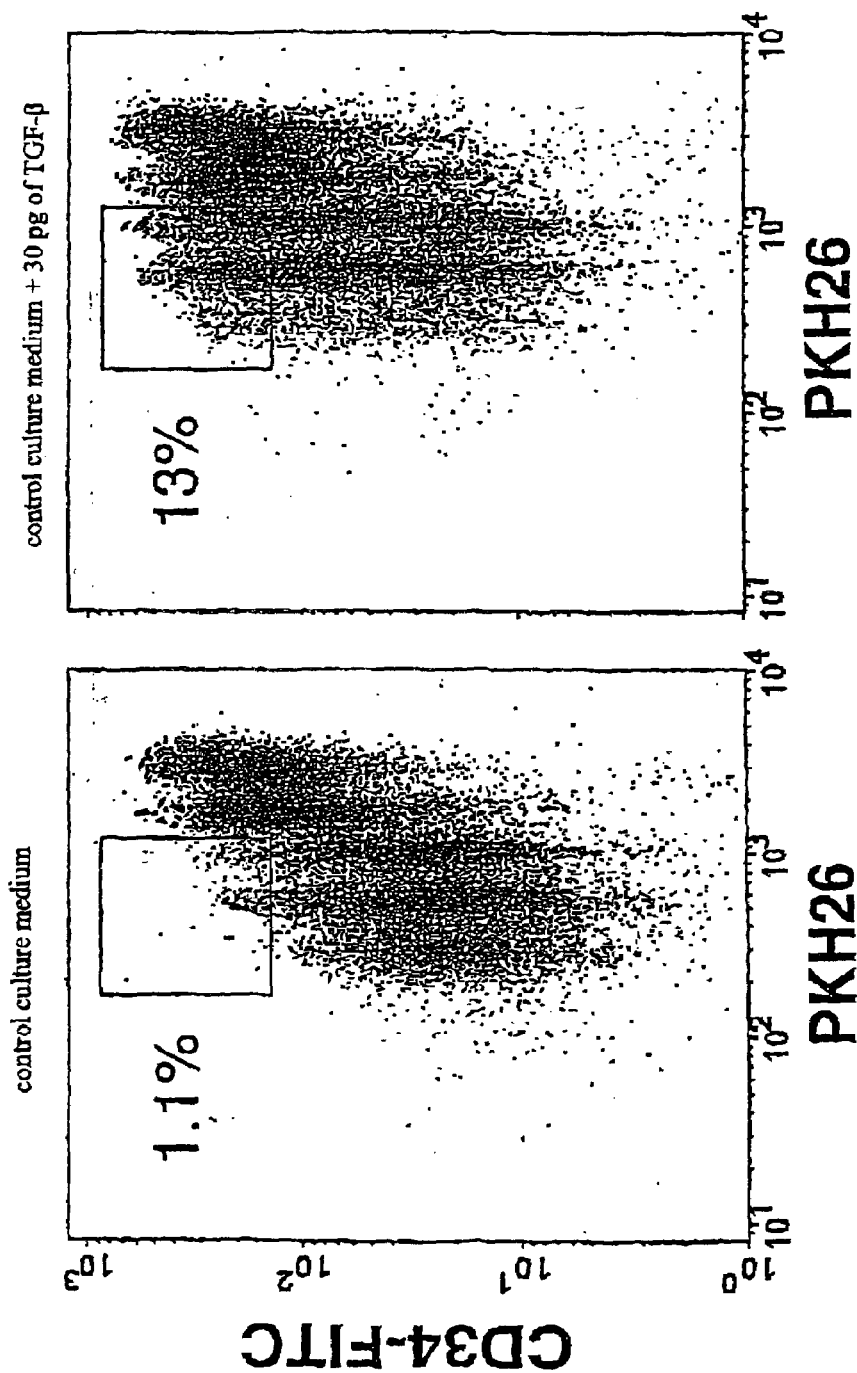

The present invention relates to a process for the multiplication of stem cells. The invention particularly relates to a process which allows, at the same time, the said stem cells to multiply rapidly and to be maintained in a non-differentiated state.

Current cultures which allow stem cells to be maintained in a non-differentiated state, and in particular hematopoietic stem cells, and/or allow them to be multiplied, are long-term cultures in which the cells divide very slowly. More particularly, cultures which allow, for example, self-renewal (multiplication to identical cells) of stem cells, in particular hematopoietic stem cells, are solely cultures on medullary stroma or cultures with slow multiplication in the absence of medullary stroma.

As regards more particularly long-term cultures on medullary stroma, there may be mentioned cultures of the Dexter type, in which stem cells, in particular hematopoietic stem cells, develop on a medullary stroma, which allows only few cytokines to be used but causes slow division of the cells (and therefore slow multiplication of the cells) in the presence of a mixture of progenitors with mature hematopoietic and stromal cells.

Furthermore, unlike mice, in humans, stem cells are not maintained on the stroma long term.

As regards long-term cultures in the absence of medullary stroma the Piacibello culture system may be mentioned. In this culture system (Piacibello et al. 1997 Blood), $CD34^+$ cells containing hematopoietic stem cells are seeded in an amount of 20,000 cells per ml, and every week half of the culture is removed and replaced by fresh medium. After two weeks the number of cells doubles at a rate of once a week for several months. During the first two weeks of the Piacibello culture there is a high loss of $CD34^+$ cells, which stabilizes at less than 2%.

The current cultures are therefore not very compatible with production of stem cells, maintaining their non-differentiated and multipotent character, for clinical or biotechnological purposes.

In addition, no inhibitor of differentiation of stem cells which allows satisfactory continuous self-renewal is known to date.

One of the main objects of the invention is to provide a process for culture of stem cells which enables human stem cells to be obtained in a non-differentiated state rapidly and in a significant amount.

One of the objects of the invention is to provide a rapid process for culture of stem cells without medullary stroma which allows the culture volumes to be reduced.

One of the other objects of the invention is the use of stem cells obtained in this way to reconstitute tissue and transplant organs.

The invention relates to the use of an inhibitor of cell development in a controlled manner to maintain the non-differentiated state of stem cells, in particular human stem cells, while allowing their cell division.

The present invention emerges from the discovery made by the inventors that under certain conditions an inhibitor of cell development may also be an inhibitor of cell differentiation of stem cells. In this respect, TGF-β (transforming growth factor), previously known as an inhibitor of cell development of stem cells, and in particular hematopoietic stem cells or primitive hematopoietic progenitors, is found to be, according to the invention, an inhibitor of cell differentiation.

The expression "inhibitor of cell development" encompasses at the same time any substance which inhibits cell proliferation and/or cell growth and/or cell differentiation.

The expression "inhibitor of cell proliferation" also means inhibitor of cell division or inhibitor of the cell cycle.

The expression "use of an inhibitor of cell development in a controlled manner" means that the inhibitor of cell development is used in a modifiable manner in order to allow:

(a) cell division of stem cells if this is desired, while maintaining the non-differentiated state of the said stem cells in the course of or at the end of the cell division, or (b) inhibition of cell development of stem cells if this is necessary to inhibit cell differentiation of the said stem cells.

The expression "use of an inhibitor of cell development in a controlled manner" means, in other words, that the inhibitor of cell development can be used in such conditions that the stem cells are brought out of their resting state in order to divide under controlled conditions preventing differentiation.

The expression "stem cells" means immature cells, or cells which are not differentiated (or non-differentiated), or primitive cells, or pluripotent cells or multipotent cells.

The stem cells advantageously used according to the invention are human stem cells chosen from the group consisting of embryonic stem cells at the origin of somatic stem cells, and/or stem cells/somatic progenitors themselves at the origin of blood and/or various solid tissues such as the skin, the liver, the pancreas, the heart, the kidney, bone or nerve tissue.

The expression "embryonic stem cells at the origin of somatic stem cells" is defined, for example, as a cell which can produce any one of the somatic stem cells.

The expression "somatic stem cells" is defined, for example, as a cell which can produce a specific tissue.

The stem cells according to the invention are, in particular, human hematopoietic somatic stem cells, also called primitive hematopoietic progenitors.

According to an advantageous embodiment, the inhibitor of cell development advantageously used according to the invention is chosen from the group consisting of products of genes which control cell development with respect to cell differentiation and/or cell division, inhibitors of cycline-dependent kinases, factors which control apoptosis or ageing, and cytokines (such as interferons or TGF-β). The term "cytokines" means all the growth factors, even if these factors can also act as growth inhibitors under certain conditions.

As products of genes which control cell development with respect to cell differentiation and/or cell division, growth factors, cytokines and the product of genes controlling differentiation, ageing or apoptosis can in particular be mentioned.

As inhibitors of cycline-dependent kinases, the retinoblastoma gene and the genes P15, P16, P21 and P27 can in particular be mentioned.

The retinoblastoma gene is a tumour suppresser gene (anti-oncogene)

The genes P15, P16, P21 and P27 inhibit the cell cycle.

As a factor which controls apoptosis, the genes bcl-2, bax and fas can in particular be mentioned.

As a factor which controls ageing there may be mentioned in particular telomerase.

As cytokines which can be inhibitors of cell development, interferons and in particular TGF-β can in particular be mentioned.

According to an advantageous embodiment, the invention relates to the use of an inhibitor of cell development as defined above in sequential combination with an anti-inhibitor of cell proliferation to initiate a number of cell divisions ranging from 1 to about 100, in particular 1 to about 10, and in particular to initiate a single cell division, while maintaining the non-differentiated state of stem cells, in particular human stem cells.

The expression "sequential combination" means that the anti-inhibitor of cell proliferation is not used simultaneously with the inhibitor of cell development.

According to an advantageous embodiment, the invention relates to a process for the multiplication of stem cells in a culture medium, in particular human stem cells, characterized in that it comprises:

a stage in which the stem cells, in particular human stem cells, in the resting state are brought out of their resting state by neutralization of the effect of an inhibitor of cell development, and in particular an inhibitor of cell proliferation, produced by the cells and/or present in the culture medium, so that there is initiation of a number of cell divisions ranging from 1 to about 100, in particular 1 to about 10, and in particular a single cell division, and a stage in which the stem cells, in particular human stem cells, obtained in the preceding stage are inhibited in their differentiation with the aid of an inhibitor of cell development.

The invention also relates to a process for the multiplication of stem cells in a culture medium, in particular human stem cells, characterized in that it comprises:

a stage according to which the stem cells, in particular human stem cells, in the state of division are prevented from entering into a state of differentiation with the aid of an inhibitor of cell development, and a stage according to which the stem cells, in particular human stem cells, obtained in the preceding stage are returned to their state of division by neutralization of the effect of an inhibitor of cell development, and in particular an inhibitor of cell proliferation, so that there is initiation of a number of cell divisions ranging from 1 to about 100, in particular 1 to about 10, and in particular a single cell division.

The multiplication process according to the invention is characterized in that in the course of and at the end of the said process, the stem cells multiplied in this way are maintained in a non-differentiated state.

According to the invention, the expression "multiplied stem cells" has the same meaning as the expression "amplified stem cells". Furthermore, the expression "multiplication process" has the same meaning as the expression "amplification process".

The resting state of cells means that the cells are not differentiating and are not dividing.

According to an advantageous embodiment, the stem cells multiplied by the multiplication process of the invention are human stem cells chosen from the group consisting of embryonic stem cells at the origin of somatic stem cells, and the somatic cells themselves at the origin of blood and/or various solid tissues, such as the skin, the liver, the pancreas, the heart, the kidney, bone or nerve tissue.

The multiplication process according to the invention is characterized in that the stem cells, in particular human cells, are present in a cell concentration of about 1 to about $10^{10}$ cells per ml, and in particular in a concentration ranging from about $10^3$ to about $10^{10}$ cells per ml, and more particularly about $10^4$ to about $10^9$ cells per ml.

It should be pointed out that the present invention applies both to human cells and to animal cells.

In the multiplication process of the invention, the inhibitor of cell development is synthesized by the stem cells, in particular human stem cells, and/or is added to the culture medium containing the stem cells, in particular human stem cells.

The said inhibitor of cell development is synthesized by the stem cells and/or is added to the culture medium:

(a) before the first cell division, and
(b) in the course of or at the end of a division cycle (if the said cells are in the state of division beforehand).

If the inhibitor of cell development is synthesized by the stem cells, it may or may not be secreted.

The amount of inhibitor of cell development synthesized by the stem cells or added to the culture medium must be sufficient for the said cells (a) to be maintained in their resting state before the first cell division and (b) to be placed in the resting state if they were in the state of division beforehand.

The amount of inhibitor of cell development synthesized by the stem cells may vary from 0.01 pg to 1 mg/ml in the culture medium, and in particular 0.1 pg to 10 ng/ml.

The amount of inhibitor of cell development added to the culture medium may vary from 0.1 pg to 1 mg/ml in the culture medium, and in particular 1 pg to 10 ng/ml.

According to an advantageous embodiment, the multiplication process according to the invention is characterized in that the inhibitor of cell development is chosen from the group consisting of gene products which control cell development with respect to cell differentiation and/or cell division, inhibitors of cycline-dependent kinases, factors which control apoptosis or ageing, and cytokines (such as interferons and TGF-$\beta$).

The products of genes which control cell development with respect to cell differentiation and/or cell division, inhibitors of cycline-dependent kinases, factors which control apoptosis or ageing and cytokines are, in particular, those described above.

According to an advantageous embodiment, the inhibitor of cell development is present in a low concentration in the culture medium containing the stem cells, and in particular in a concentration ranging from about $10^{-10}$ mg/ml to 1 mg/ml.

The multiplication process according to the invention is characterized in that the neutralization of the effect of the inhibitor of cell development, and in particular the inhibitor of cell proliferation, present in the culture medium is effected by:

addition to the culture medium of an anti-inhibitor of cell proliferation, and/or withdrawal from the culture medium of the inhibitor of cell development, and in particular the inhibitor of cell proliferation.

The neutralization of the effect of the inhibitor of cell development allows the stem cells to leave their resting state and to initiate at least one division.

Preferably, if the inhibitor of cell development is synthesized without being secreted by the stem cells, the effect of the said inhibitor is neutralized by addition to the culture medium of an anti-inhibitor of cell proliferation which can penetrate into the cell, such as an antisense oligonucleotide.

However, if the inhibitor of cell development is secreted by the stem cells or if the said inhibitor is added to the culture medium the effect of the said inhibitor is neutralized either by addition to the culture medium of an anti-inhibitor of cell proliferation or by withdrawal from the culture medium of the inhibitor of cell development.

The withdrawal of the inhibitor of cell development from the culture medium can in particular be effected with the aid of blocking antibodies or by washing in order to neutralize the said inhibitor.

The amount of inhibitor of cell development withdrawn from the culture medium containing the stem cells must be sufficient for there to be initiation of a number of cell division ranging from 1 to about 100, in particular 1 to about 10, and in particular a single cell division.

The amount of inhibitor of cell development withdrawn from the culture medium varies from 0.01 pg to 1 ng/ml, and in particular 0.1 pg to 10 ng/ml The inhibitor of cell development withdrawn from the culture medium belongs in particular to the group consisting of cytokines and antisense oligonucleotides which block the expression of development genes.

The amount of anti-inhibitor of cell proliferation added to the culture medium containing the stem cells must be sufficient for there to be initiation of a number of cell divisions ranging from 1 to about 100, in particular 1 to about 10, and in particular a single cell division.

The amount of anti-inhibitor of cell proliferation added to the culture medium varies from 0.1 µg to 10 mg/ml for the blocking antibodies or from 0.01 µM to 1 mM of antisense oligonucleotide in the culture medium, and in particular 1 µg to 100 µg/ml for the blocking antibodies or 0.1 µM to 100 µM of antisense oligonucleotides.

The anti-inhibitor of cell proliferation is chosen from the group consisting of antisense oligonucleotides or blocking antibodies and in particular anti-TGF-β.

According to an advantageous embodiment, the multiplication process according to the invention is characterized in that the anti-inhibitor of cell proliferation is present in a concentration ranging from about $10^{-18}$ t about $10^{-3}$ g/ml, in particular 0.1 to 20 µg/ml, and in particular $4.10^{-6}$ g/ml (4 µg/ml).

The process according to the invention for the multiplication of stem cells, in particular human stem cells, is characterized in that it comprises, in order to obtain a sufficient number of stem cells maintained in the non-differentiated state, a total number of division cycles (or states of division) of between 1 to 100 cycles, in particular between 5 to 20 cycles, and in particular 10 cycles.

According to an advantageous embodiment, the total duration of all the resting states of the multiplication process according to the invention varies from 1 hour to 3 years, in particular 20 hours to 200 hours, and the total duration of all the division cycles of the multiplication process according to the invention varies from 10 hours to 3 years, and in particular 20 hours to 200 hours.

According to an advantageous embodiment, the multiplication process according to the invention is characterized in that the duration of a single resting state ranges from about 1 hour to 3 years, and is in particular about 6 hours to 72 hours, and in that the duration of a single division cycle ranges from about 6 hours to 3 years, and is in particular 6 hours to 24 hours.

The total duration of the multiplication process according to the invention comprising all the states of resting and of division ranges from 1 day to 3 years, and is in particular 1 day to 15 days.

According to an advantageous embodiment, the total of all the cycles of resting and division of a multiplication process lasts 1 to 15 days, and the proposed applications are cell therapy.

According to another embodiment, the total of all the cycles of resting and division of a multiplication process lasts 1 day to 3 years, and the proposed applications are of an experimental order.

A process which lasts 3 years allows, for example, experiments of long duration to study senescence.

According to an advantageous embodiment, the process according to the invention for the multiplication of stem cells, and in particular human somatic stem cells, enables an amplification of stem cells by a factor of between about 2 to about $10^{12}$, and in particular 2 to about $10^4$, to be obtained.

The multiplication process according to the invention thus allows a number of stem cells amplified and maintained in the non-differentiated state 2 to $10^{12}$ times higher than the initial number of non-differentiated stem cells to be obtained.

According to an advantageous embodiment, the culture medium of the multiplication process according to the invention contains hematopoietic stem cells and comprises one or more cytokines (added to the culture medium) chosen from the groups consisting of interleukins and CSF, the said cytokines being present in a concentration ranging from about $10^{-8}$ µg/ml to about 1 mg/ml, and in particular about $10^{-5}$ µg/ml to 0.1 µg/ml, and where appropriate other growth factors.

As cytokines which can be added to the culture medium there may be mentioned in particular interleukins, such as IL 1 to IL 16, CSF (colony-stimulating factors), such as GM-CSF (granulocyte and monocyte colony-stimulating factor), GCSF (granulocyte colony-stimulating factor), MCSF (monocyte colony-stimulating factor), SF (Steel factor), TPO (thrombopoietin) or FL (Flt-3 ligand).

Growth factors other than interleukins and CSF can be used.

The process according to the invention for the multiplication of stem cells, and in particular human somatic stem cells, is more particularly characterized in that it comprises the following stages:

a) initiation of a first cycle of division of non-differentiated embryonic or somatic stem cells in a culture medium, and in particular of hematopoietic somatic stem cells, by seeding the said non-differentiated stem cells in the resting state in a high initial cell concentration, in particular in a concentration ranging from $10^3$ to $10^{10}$ cells per nil, in the presence of one or more cytokines, and by neutralization of the effect of the inhibitor of cell development, and in particular the inhibitor of cell proliferation, present in the culture medium so that the above-mentioned cells leave their resting state by the initiation of a first cell division, b) return to resting of the non-differentiated embryonic or somatic stem cells obtained in the preceding stage with the aid of an inhibitor of cell development, the said inhibitor being synthesized by the said stem cells or being added to the culture medium, c) if appropriate washing of the non-differentiated embryonic or somatic stem cells obtained in the preceding stage in order to remove the catabolites and the inhibitor of cell development, and in particular the inhibitor of cell proliferation which may be present in the culture medium, d) if appropriate dilution of the non-differentiated embryonic or somatic stem cells obtained in the preceding stage in order to maintain an optimum cell concentration ranging from about 100 to $10^{10}$ cells per ml, e) successive repetition of the cycles of division and resting described above until the amplification factor of the cells is sufficient to obtain the number of desired stem cells, and in particular 2 times to about $10^{12}$ times the number of initial non-differentiated embryonic or somatic stem cells, which corresponds to a total duration of the multiplication process of about 1 day to 3 years, and in particular 1 day to 15 days, f) stopping of the multiplication of non-differentiated embryonic or somatic stem cells to store them, use them or cause them to differentiate in vitro.

The methods of the various stages of the process according to the invention for the multiplication of stem cells are those already described above.

The amount of anti-inhibitor of cell proliferation added to the culture medium or the amount of inhibitor of cell development withdrawn from the culture medium containing the stem cells must thus be sufficient for there to be initiation of a first cell division.

According to a preferred embodiment, the inhibitor of cell development is TGF-β; TGF-β is synthesized by hematopoietic somatic stem cells themselves in an amount ranging from 0.01 pg to 1 ng/ml.

The TGF-β is then neutralized by addition to the culture medium of an anti-inhibitor of cell proliferation: anti-TGF-β. Anti-TGF-β is added in an amount ranging from 0.1 to 100 µg/ml of antibodies or 0.1 µM to 10 µM of oligonucleotides.

The return to resting of the hematopoietic somatic stem cells, in particular described in stage b) above, is obtained by the TGF-β synthesized by the said stem cells themselves (or other added inhibitors).

The washing stage (c) described above allows in particular neutralization of the inhibitor TGF-β formed in the course of or at the end of a preceding division cycle in order to allow the following division.

The dilution stage (d) described above maintaining an optimum cell concentration allows at the same time:

rapid return to the resting state of the stem cells due to a rapid synthesis by the said cells of the inhibitor of cell development, in particular TGF-β, no less rapid a division of the stem cells after each resting state, in the presence of the anti-inhibitor of cell proliferation, in particular anti-TGF-β.

TGF-β slows down the process of differentiation of stem cells throughout the multiplication process, that is to say in the course of and at the end of the various cycles of resting and division.

The stopping stage f) described above can be effected by washing the said stem cells multiplied in this way, by freezing them, or by placing them in a differentiation medium.

The differentiation medium in which the stem cells multiplied and maintained in a non-differentiated state in this way by the process of the present invention are placed is chosen according to the tissue or organ it is intended to reconstitute.

For example, if the intention is to obtain erythroid cells, a culture medium comprising erythropoietin (EPO) will be used.

The multiplication process according to the invention allows significant productions of stem cells to be obtained, the said stem cells being maintained in a non-differentiated state in the course of the various cycles of resting and division of the said process. Significant productions of immature cells are obtained in this way in a reduced volume.

The present invention relates to the use of non-differentiated and amplified human stem cells such as are obtained by the process of the invention described above to reconstitute human blood and/or human solid tissue or organs.

The non-differentiated and amplified human stem cells such as are obtained by the process of the invention can thus be used in particular to amplify insufficient samples of blood from the umbilical cord, bone marrow or peripheral blood, or for transplantation of hematopoietic stem cells.

The non-differentiated and amplified human stem cells such as are obtained by the process of the invention can also be used for studies on the human genome (expression and functioning of the genes of human development).

Legend to the Figures

FIGS. 1A and 1B show the effect of TGF-β on the maintenance of the non-differentiated state of CD34$^+$ cells.

The stain PKH26 which attaches itself to the membrane of cells allows the number of divisions which the cell has effected to be determined: after one doubling of the cell the intensity of the stain is divided by 2, after 2 doublings by 4 etc. Various populations displaced to the right are thus obtained.

Under culture conditions without TGF-β, (20,000 cells per ml) (FIG. 1A), the cells divide, and after 3 days the cells which have divided more than once contain only 1.1% of CD34$^{+high}$ cells.

Under culture conditions according to the invention, since the concentration of TGF-β is higher (30 pg/ml TGF-β) (FIG. 1B), a higher percentage of CD34$^{+high}$ cells is observed.

EXAMPLE

Process for the Multiplication of Hematopoietic Stem Cells

Materials and Methods

The stem cells used in the example below are more particularly human hematopoietic somatic stem cells originating from the blood of the umbilical cord and characterized by the membrane marker CD34+. In the following, the said cells will be called "CD34+ cells".

1) Marking of CD34+ Cells

The CD34+ cells are diluted in PBS (phosphate-buffered saline)/BSA (bovine serum albumin) (0.2%) and incubated with anti-CD34+ antibodies conjugated with FITC (fluoroisothiocyanate) (clone 8G12; Becton Dickinson, San José, CA) for 30 minutes at 4° C. and then washed 2 times in PBS/BSA. The control consists of cells incubated with non-specific IgG1 conjugated with FITC.

To detect the stain allowing the proliferation of the cells to be monitored, the CD34+ are marked with the stain PKH26 (Sigma, France) in accordance with the manufacturer's instructions.

The cells with an average intensity of PKH26 are screened in a window representing about 10% of the complete width. This corresponds to about 20% of the CD34+ cells. Four aliquots of 400 cells are used in the HPP-Q test. The remainder of the resting cells and the cells which proliferate are screened and cultured in semi-solid medium. Calibrated beads (Coulter-Beckman) are used to standardize the analyses between day 0 and day 3.

Description of the HPP-Q Test (High Proliferative Potential-Quiescent Cell)

The HPP-Q test allows verification that the inhibitor of cell development, in particular TGF-β, is maintaining the stem cells, in particular hematopoietic stem cells, at rest.

More particularly, the HPP-Q test consists of determination of the degree of maturity of stem cells, in particular hematopoietic stem cells, and is characterized in that it comprises the following stages:

a first collection of stem cells, in particular hematopoietic stem cells, is cultured in a medium suitable for their culture, the said medium containing no means of blocking for at least one inhibitor of cell development, such as TGF-β, for about 14 to about 28 days, preferably 18 days, a second collection of stem cells, in particular hematopoietic stem cells, of the same nature and the same degree of maturity as those mentioned above is cultured in a suitable medium comprising means of blocking for at least one inhibitor of cell development, these means of blocking being present in the culture medium in an effective concentration, 18 days after the start of culture of each of the two collections of stem cells, the number and the nature of the colonies and the difference in the totals of colonies of high proliferative potential (HPP-CFC=progenitor forming a colony of high proliferative potential, HPP-MEG=megakaryocyte progenitor of high proliferative potential, HPP-GEMM=granulocyte erythrocyte monocyte megakaryocyte progenitor of high proliferative potential) respectively in that of the second collection and that of the first collection are compared.

The evaluation of the maturity or immaturity of the stem cells corresponds to the following observation.

After 18 days the number and nature of the colonies are observed under a microscope: the number of mixed colonies made up of cells of the red line and of one or more types of the white line is counted. The number of mixed colonies is higher if the cell population cultured is immature, that is to say made up of younger cells, some of which are at rest. On the other hand, the more immature, or even at rest, the cell which has produced the colony, the higher its potential for proliferation, and therefore the colony originating from this cell, once activated, will be larger in size.

2) Culture of CD34+ Cells

CD34+ cells were seeded at a cell concentration of $10^6$ cell per ml in 24-well culture plates in an amount of 1 ml per well on day D0. The said cells were seeded in a medium without serum and comprising cytokines and an inhibitor of TGF-β (anti-TGF-β).

| "Medium": | |
|---|---|
| SBA (medium without serum with albumin) + | |
| SF (Steel factor) | 10 ng/ml |
| TPO (thrombopoietin) | 10 ng/ml |
| FL (ligand FLt3) | 50 ng/ml |
| 1L6 (interleukin 6) | 10 ng/ml |
| Anti-TGF-43 | 4 µg/ml |

The CD34+ cells are incubated at 37° C. in an atmosphere with 5% $CO_2$ and humidity saturation at 97%.

Every 2 days the volume of the culture is measured, the number of CD34+ cells is counted and the viability of the said cells is determined.

After the number of CD34+ cells contained in the culture has been counted, the volume necessary to leave only $10^6$ cells per well is removed.

The volume, cytokines or growth factors and inhibitor of TGF-β in the medium is readjusted.

Every 8 days screening is carried out to evaluate the $CD34^+$ and $CD38^-$ cells and the proliferative capacity of the $CD34^+$ cells is evaluated in the HPP-Q test.

The results of the HPP-Q test are confirmed regularly by a test in immunodeficient mice (SCID-NOD).

The protocol of the process according to the invention allows cells to be cultured in a microbioreactor which keeps the conditions of the media constant as regards catabolites and anabolites (excluding cytokines and inhibitors).

Seeding of the CD34+ cells in a high cell concentration allows a bioreactor to be created at a high cell concentration, and thus allows the culture volumes to be reduced.

Bioreactor or Microbioreactor Principle

A microbioreactor comprises a culture chamber of a size suitable for the number of cells and their cell density (1 to 100 ml), separated from a dialysis chamber by a membrane, and where appropriate from a gas chamber by another membrane, to keep the constituents of the medium constant.

Microdetectors allow control of various parameters in the culture chamber: pH, $CO_2$, $O_2$, glucose, lactate etc.

Inlets and outlets allow renewal or modification of the culture media, or addition or withdrawal of cells.

The entire microbioreactor can be automated by pumps and computerized programmers.

The invention claimed is:

1. A method for maintaining a non-differentiated state of human stem cells, while allowing cell division of said human stem cells, comprising repeatedly administering to human stem cells in a cell concentration of about 1 to about $10^{10}$ cells per ml an effective amount of an inhibitor of cell proliferation of cell development in sequential combination with an anti-inhibitor in a controlled manner to maintain the non-differentiated state of stem cells, while allowing their cell division until the amplification of the cells is sufficient to obtain a pre-determined number of cells, wherein said anti-inhibitor is anti-TGFβ in an amount of 0.1 µg to 10 mg/ml, and wherein said inhibitor is TGFβ in an amount of 0.01 pg/ml to 1 mg/ml and said human stem cells are hematopoietic stem cells.

2. The method according to claim 1, further comprising the following steps:
   a) initiating a first cycle of division of said non-differentiated stem cells, by seeding non-differentiated stem cells in a resting state in an initial cell concentration, in the presence of one or more cytokines, and neutralizing the effect of an inhibitor of cell development present in the culture medium so that said cells leave their resting state by the initiation of a first cell division,
   b) returning said cells to a resting state by treating said cells with an inhibitor of cell development, said inhibitor being synthesized by said stem cells or being added to the culture medium,
   c) optionally washing said cells obtained in the preceding stage to remove catabolites and the inhibitor of cell development,
   d) optionally diluting said cells obtained in the preceding stage to maintain an optimum cell concentration ranging from about 100 to $10^{10}$ cells per ml,
   e) repeating the cycles of division and resting described above until the amplification factor of the cells is sufficient to obtain the number of said cells, and
   f) stopping of the multiplication of non-differentiated stem cells to store them, use them or cause them to differentiate in vitro.

3. The method according to claim 2, wherein neutralization of the effect of the inhibitor of cell development, present in the culture medium is effected by
   addition to the culture medium, in a suitable amount, of an anti-inhibitor of cell proliferation, and
   withdrawal from the culture medium of the inhibitor of cell development.

4. The method according to claim 2, wherein the duration of a single resting state ranges from 1 hour to 3 years and in that the duration of a single division cycle ranges from about 6 hours to 3 years.

* * * * *

UNITED STATES PATENT AND TRADEMARK OFFICE
CERTIFICATE OF CORRECTION

PATENT NO.       : 7,601,534 B1                                    Page 1 of 1
APPLICATION NO.  : 09/980484
DATED            : October 13, 2009
INVENTOR(S)      : Hatzfeld et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1161 days.

Signed and Sealed this

Fifth Day of October, 2010

David J. Kappos
*Director of the United States Patent and Trademark Office*